(12) United States Patent
Sasaki (10) Patent No.: US 6,611,321 B1
(45) Date of Patent: Aug. 26, 2003

(54) METHOD OF MEASURING DISTRIBUTION OF INTERNAL REACTIVE INDEX FOR OPTICAL FIBER PREFORM AND MEASURING DEVICE

(75) Inventor: Issei Sasaki, 2-7, Maeda 9-jo 17-chome, Teine-ku, Sapporo-shi (JP)

(73) Assignees: Issei Sasaki (JP); Seiko EG&G Co., Ltd.

( * ) Notice: Subject to any disclaimer, the term of this patent is extended or adjusted under 35 U.S.C. 154(b) by 0 days.

(21) Appl. No.: 09/412,500

(22) Filed: Oct. 5, 1999

(30) Foreign Application Priority Data

Dec. 10, 1998 (JP) .......................................... 10-289445

(51) Int. Cl.⁷ .............................................. G01N 21/00
(52) U.S. Cl. ................................................... 356/73.1
(58) Field of Search ....................... 356/73.1, 124–128; 385/24, 12–14

(56) References Cited

U.S. PATENT DOCUMENTS 4,515,475 A * 5/1985 Payne et al. ................ 356/73.1
4,519,704 A    5/1985 Mansfield et al. .......... 356/73.1
4,664,516 A    5/1987 Coppa et al. ............... 356/73.1
5,365,329 A   11/1994 Svendsen .................... 356/73.1

FOREIGN PATENT DOCUMENTS

JP      04095847      3/1992
JP      08201221      8/1996

* cited by examiner

Primary Examiner—Tu T. Nguyen
(74) Attorney, Agent, or Firm—Adams & Wilks (57) ABSTRACT

The internal refractive index distribution of an optical fiber preform is measured by providing a generally-cylindrical optical fiber preform having an uneven internal refractive index distribution. A picture image is placed at one side of the optical fiber preform, and a deflected picture of the picture image is photographed through the optical fiber preform using a photographing unit placed at the other side of the optical fiber preform. A deflection function is obtained by analyzing the deflected picture of the picture image. The internal refractive index distribution of the optical fiber preform is measured in accordance with the deflection function obtained.

29 Claims, 13 Drawing Sheets

Fig. 12

METHOD OF MEASURING DISTRIBUTION OF INTERNAL REACTIVE INDEX FOR OPTICAL FIBER PREFORM AND MEASURING DEVICE

BACKGROUND OF THE INVENTION

The present invention relates to a method of measuring a distribution of internal refractive index for a preform of an optical fiber, and to a measuring unit for performing the method.

The optical fiber is important as an information medium supporting intelligent society, and performance of the optical fiber depends on a shape of the refractive index distribution (hereinafter "reactive index distribution") formed inside of the fiber. A measuring technique for inspecting the formed structure is essential to the precise control technique of obtaining a shape measurement of the reactive index distribution. In this case, it is hard to measure the inside of the optical fiber in detail and the measurement is large in error because of the extremely thin diameter of the fiber. Therefore, the fiber is ordinarily measured at a preforming step (optical fiber preform, hereinafter called preform) which is the intermediate product before wire drawing the optical fiber. The structure of the reactive index for the optical fiber is formed at the inside of the preform by a chemical vapor deposition (CVD) method, a vapor-phase axial deposition (VAD) method, and so on. As the structure of the preform and the structure of the optical fiber are similar in shape, it is considered that the result of measuring the preform can be applied for the optical fiber by reduction of the scale. The optical fiber is produced by softening the preform with heat and by drawing the optical fiber to provide it with a predetermined diameter.

In the conventional method for measuring reactive index of the optical fiber preform, deflection function is found by permeating the measured object with parallel rays or thin laser radiation and by measuring reflection of rays received by distribution of internal reactive index.

However, in the measured object being large in change of reactive index such as high NA (number of opening) optical fiber preform, angle of deflection of transmitted light becomes large so that the light does not come in sight of a detector. Stated otherwise, the ray being large in angle of deflection is hard to detect and leaks from measurement so that accuracy of measurement decreases sharply.

The present invention is done at the view of the above-mentioned problem of the prior art, and an object of the present invention is to provide a method of measuring distribution of an internal reactive index of an optical fiber preform enabling to measure distribution of reactive index of a high NA optical fiber preform and, to a measuring device for performing the method. Particularly, the present invention provides a new measuring technique applicable to preforms which are hard to measure by the conventional method.

SUMMARY OF THE INVENTION

In the method of measuring a distribution of internal reactive index for an optical fiber preform according to the present inventions, a picture image is located behind the optical fiber preform being cylindrical and having uneven distribution of reactive index at inside of the material, and a deflected picture of said picture image is photographed through the optical fiber preform. By analyzing the deflected picture of said picture image, a deflection function is found, and a distribution of the reactive index of the optical fiber preform is found based on the deflection function.

In this case, it is desirable that the deflection function is found by a method of ray tracing from the deflected picture of the picture image.

It is desirable to light the picture image with an incoherent light source.

It is desirable to have a pattern having position data in the picture image where the light generates for the picture image.

A binary picture image of right-angled triangle can be used for such picture image. In this case, it is desirable to find a border line of variable density picture image determining threshold values different partly adapting to condition of the picture image, to find entire the border line combining the found border line, and to find a distribution of deflection of the picture from the whole border line.

A binary picture image of an isosceles triangle or picture image which hue or wavelength thereof changes continuously can be used for the picture image.

In the measuring device of distribution of internal reactive index for the optical fiber preform according to the present invention, a picture image is located behind the optical fiber preform being cylindrical and a having uneven distribution of reactive index at inside of the material, and a deflected picture of said picture image is photographed through the optical fiber preform. By analyzing the deflected picture of said picture image, a deflection function is found, and distribution of reactive index of the optical fiber preform is found based on the deflection function. The measuring device is characterized by comprising a picture image of pattern having position data, an incoherent light source lighting the picture image, a supporting unit for supporting the optical fiber preform in front of the picture image, a photographing unit for photographing the deflected picture of said picture image through the optical fiber preform, and an arithmetic and logic unit for finding a deflection function from the photographed deflected picture and for finding a distribution of reactive index of the optical fiber preform based on the deflection function.

In this case, an incoherent light source comprises a light source and a scattering board located at the front of the light source. An electroluminescence board can be used.

The photographing unit is desirable to have a diaphragm for limiting aperture, and a mask or a space filter.

In the present invention, the picture image is located behind the optical fiber preform being cylindrical and having uneven distribution of reactive index at inside of the material, and the deflected picture of said picture image is photographed through the optical fiber preform. By analyzing the deflected picture of said picture image, a deflection function is found, and a distribution of reactive index of the optical fiber preform is found based on the deflection function. Therefore, a photographing picture image is possible so as to photograph the deflected picture if the preform is a high NA optical fiber preform and an angle of deflection of a permeating ray becomes large. Therefore, even high NA optical fiber preform difficult in measuring by the conventional method can measure the distribution of reactive index accurately, and that contributes to improvement of performance of the optical fiber so as to contribute to the development of intelligent society.

DETAILED DESCRIPTION OF THE PREFERRED EMBODIMENTS

A principle of method of measuring a distribution of internal reactive index for optical fiber preform and an embodiment according to the present invention will be described a below.

In the conventional method of measuring distribution of reactive index, a ray has been applied to a measured object at an angle of zero degree and an angle of deflection of the ray has been measured by an incline of the ray after permeating based on a direction of the applied ray. In this method, the ray deflecting widely than aperture of a detector can not be detected so as to have error.

Oppositely, by separating angle of deflection into $\phi_1$ and $\phi_2$ ($\phi_2$ is angle of incidence on measure object to optical axis and $\phi_1$ is angle of injection from the measured object to the optical axis about every ray), each angle does not become too large by dividing two even if the angle is large angle of deflection. The above-mentioned method can detect rays having large angle of deflection detected without leakage.

However, although data of generating position of rays is well known because parallel rays are used in the conventional method, the data must be measured at any time because data of the method of the present invention is variable. By introducing the new general idea of the present invention, the problem is solved. It means that a picture image is located behind the preform and deflection of the picture image looked through the preform is used. Difference with the case that the picture image is not deflected shows moving quantity of generating point of the rays and can determine the position of the generating point.

In the general expression, the method can regenerate data of position of generating point since picture image analysis by each ray has data of position of generating point. Thus, as the new problem is solved, even rays being difficult in the prior art and having large angle of deflection can be caught so as to remove cause of measuring error.

Figure 1A:
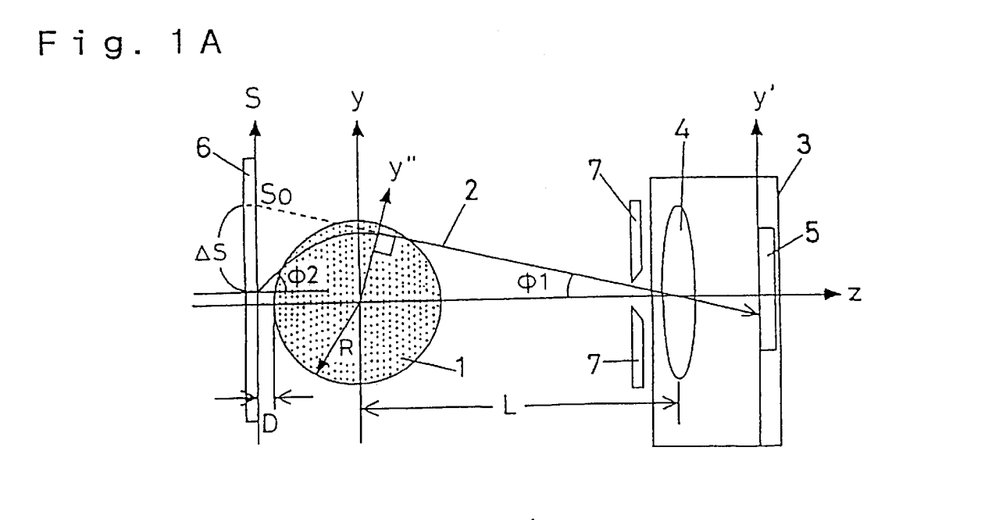
FIGS. 1A and 1B are views for describing a principle of a method of measuring a distribution of internal reactive index for optical fiber preform according to the present invention.
Figure 1B:
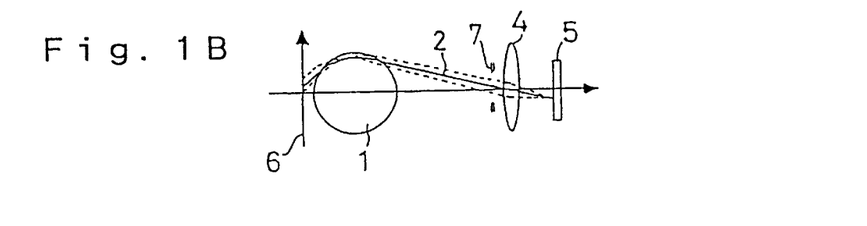

Referring FIGS. 1A and 1B, principle of the present invention will be described. FIG. 1A shows a state in which a picture image 6 is photographed by a picture image photographing unit (picture image sensor) 3 looking at the image through a measured object (optical fiber preform.) For describing, coordinate x is taken to axis direction of a preform 1, and coordinate y and coordinate z are taken each other like the figure.

A ray is generated from face of the picture image 6 as a (second) light source S is used for a generating position of the ray. The ray is applied to the picture image photographing unit 3 through a diaphragm 7 after permeating the measured object 1, and a CCD 5 in the unit photographs a projected image. In the figure, an example of the ray is shown as a ray 2. If there is not the measured object 1 or the measured object has a value of reactive index same as the circumference, the ray coming from CCD 5 ought to generate from S=$S_0$ in the figure. However if there is uneven reactive index at inside of the measured object 1, the ray 2 is deflected like the figure and it is considered that the detected ray 2 is generated from another point as the result. The picture image is photographed deflecting ΔS as the result. Then, the projected image photographing deflection of the picture image is found by analysis, and angle of deflection of the ray is presumed from the deflection this time. Angles of deflection of rays found about various rays are called a deflection function, and it is a well known arithmetic technique that a deflection function finds distribution function of reactive index numeric-transforming the deflection function (for example, Electron. Lett., 13 pp. 736–738 (1977); J. Lightwave Tech., LT-3, pp. 678–683 (1985)). It is well known to find the deflection function by measuring and to find distribution of reactive index next by a numeric process of the function.

More, particularly the present invention provides a method of measuring a reactive index of an optical fiber preform using a new technique in a process of finding a deflection function and to a measuring devices for performing the method.

Deflection function Φ (y") is given by the sum of two angle components. That is;

$$\Phi(y") = \phi_1 + \phi_2 \quad (1)$$

Here y" is distance of the ray 2 applied to the picture image photographing unit 3 from center of the measured subject (optical fiber preform), $\phi_1$ is an angle of incidence to z axis (ray axis) toward the picture image photographing unit 3, and $\phi_2$ is an angle of generation of the ray 2 from the picture image 6.

Considering that optical fiber preform 1 of the measure object ordinary keeps generally uniform internal structure to direction of x axis, it is defined that $\phi_1$ and $\phi_2$ are in the same plane, and it is presumed that S axis is parallel with y axis. Deflection quantity ΔS=$S_0$−S of the ray 2 at the plane of picture image 6 is related to angles $\Phi_1$ and $\phi_2$ of the ray 2 as follows:

$$\Delta S = a(\tan \phi_1 + \tan \phi_2) \quad (2)$$

Here $$a = (D+R) - y'' \cdot \sin\{(\phi_2 - \phi_1)/2\} \div \cos\{(\phi_2 + \phi_1)/2\} \quad (3)$$

D is a space between the measured object (optical fiber preform) 1 and the picture image 6 looked at through the object, and R is a radius of the measured object (optical fiber preform) 1. Moreover, y″ and $\phi_1$ are expressed as follows if distance from a light-intercepting lens 4 to the central axis x is represented by L;

$$y'' = L \cdot \sin \phi_2 \quad (4)$$

$$\phi_1 = \tan^{-1}(y/L) \quad (5)$$

In equation (5), as L is possible to measure and y is possible to read from the projected image photographed, $\phi_1$ can be calculated easily. In calculations of equation (2) and equation (3), $\phi_2$ can be determined if ΔS can be measured because D and R are possible to measure. Deflection function Φ(y″) therefore is obtained from $\phi_1$ and $\phi_2$ found by a ray tracing method like the above-mentioned using the equation (1.)

According to the present invention, it is new idea to write and store data distinguishing S value, that is generating position of the ray 2, at the picture image 6. In other words, the generating point of the ray 2 can be presumed by letting the ray 2 itself have position data of the generating point and by reading out the data from photographed projected image. Thus the above-mentioned matters are all possible to calculate, deflection function Φ (y″) can be determined, and distribution of reactive index is obtained converting by well-known numerical process mentioned above.

Although one ray has been described until now, geometric optics of the above-mentioned ray tracing method holds for not only one ray 2 shown in FIG. 1A. If generation from light source such as EL and so on lighting the picture image 6 does not have directivity, clarity of edge of the photographed projected image deteriorates because various rays come in the range determined by aperture of light-intercepting of the lens 4 as shown in FIG. 1B. To solve the problem, detected rays are limited in the range of paraxial rays so as to approximate well with the above-mentioned geometric optics by stopping enough the diaphragm 7 of the photographing unit 3 or by attaching a space filter or a mask selecting only rays permeating a center portion at position of main rays of the lens 4.

Figure 2A:
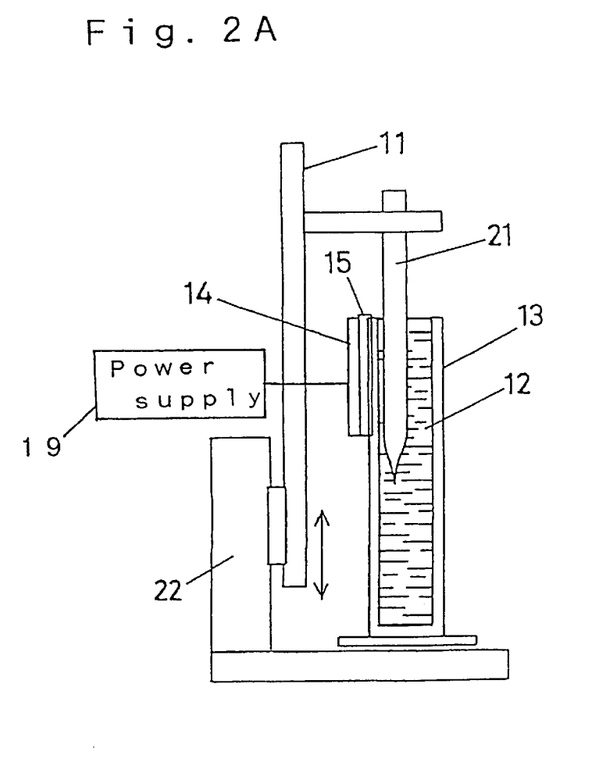
FIGS. 2A and 2B are views showing location of an embodiment embodying the method of the present invention.
Figure 2B:
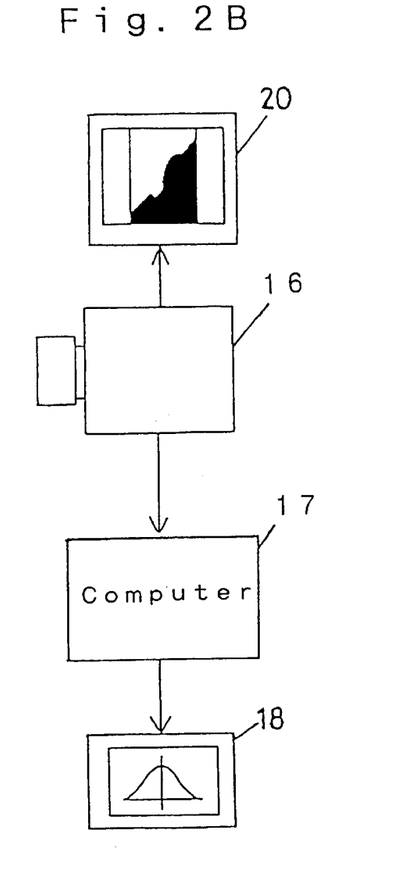
Figure 3A:
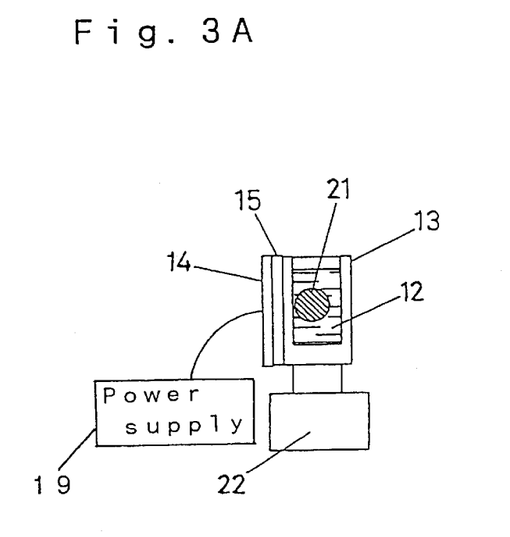
FIGS. 3A and 3B are views showing location of another embodiment embodying the method of measuring of the present invention.
Figure 3B:
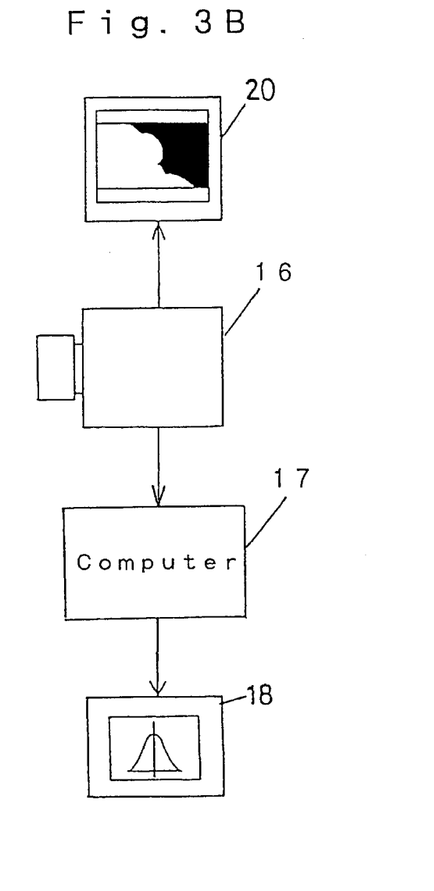

FIGS. 2A, 2B, 3A, and 3B show embodiments of devices embodying the method of the present invention. FIGS. 2A and 2B show an example in which a preform 21 is located vertically, and FIGS. 3A and 3B show examples in which a preform 21 is located horizontally. Both of FIGS. 2A and 3A are side views of the devices. In the figures, symbol 11 is a column, symbol 12 is matching liquid of reactive index, symbol 13 is a cell of matching liquid of reactive index, symbol 14 is an electroluminescence (EL) board, symbol 15 is a picture image, symbol 16 is a photographing unit, symbol 17 is a computer, symbol 18 is a display unit of the result of process, symbol 19 is a power supply for the EL, symbol 20 is a monitor of the projected image, symbol 21 is an optical fiber preform, and symbol 22 is a driving stage of x axis. In the embodiment of FIG. 2A, the preform 21 is fixed vertically at the column 11, and a part of the measured object is dipped in the cell 13 filled with the matching liquid of reactive index 12. In the embodiment of FIG. 3A, it is needed that the whole of the preform 21 or at least a measured portion is bathed in the matching liquid of the reactive index 12 and that the cell 13 of matching liquid of reactive index has a plane transparent window of a size to take out the rays without trouble though the whole of the preform 21 is bathed in the matching liquid of reactive index 12.

In any of these embodiments, the picture image 15 lighted by the electroluminescence (EL) board 14 is located behind of the preform 21 (e.g., at a first side of the preform 21), and the picture image is read into the computer 17 by the photographing unit 16 (which is located at a second side of the preform 21 opposite the first side thereof) as a digital picture image. The power supply 19 is formed for driving the EL board 14.

Figure 4A:
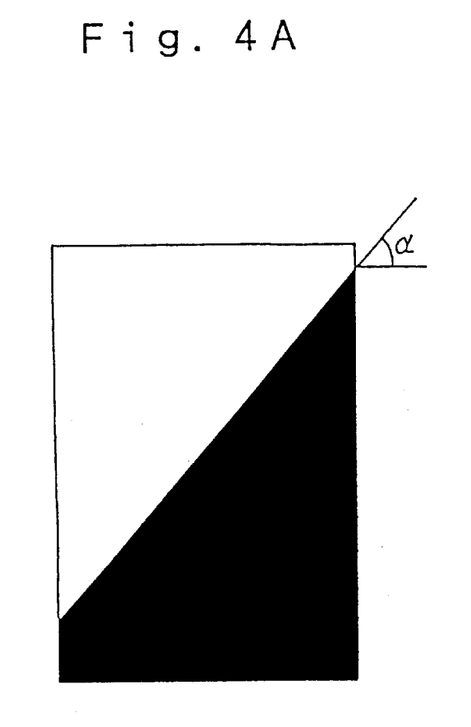
FIGS. 4A and 4B are examples of a picture image used for the method of measuring of the present invention.
Figure 4B:
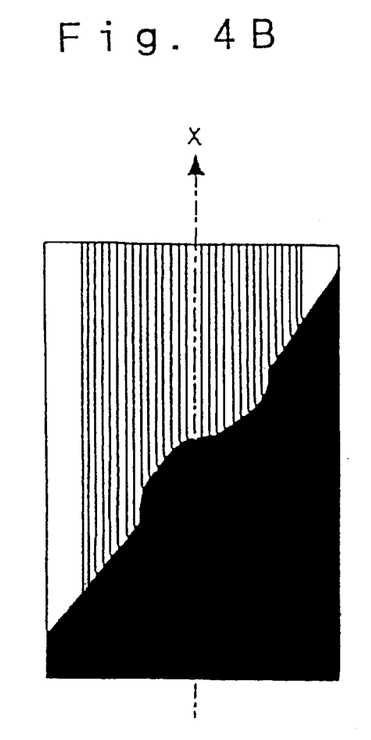

It is desirable that the pattern can distinguish clearly deflection by distribution of internal reactive index of the preform for the picture image 15. FIG. 4A describes the case in which two values (black and white) picture image of right-angled triangle is used as an example of the picture image. A portion of transformation in which dark portion projects to bright portion and a portion of transformation in which bright portion projects to dark portion appear because the border between the dark portion and the bright portion of the long side of the right-angle triangle is transformed by reactive index and deflection function is generally rotation symmetry centering the original point as shown in FIG. 4B.

Figure 4C:
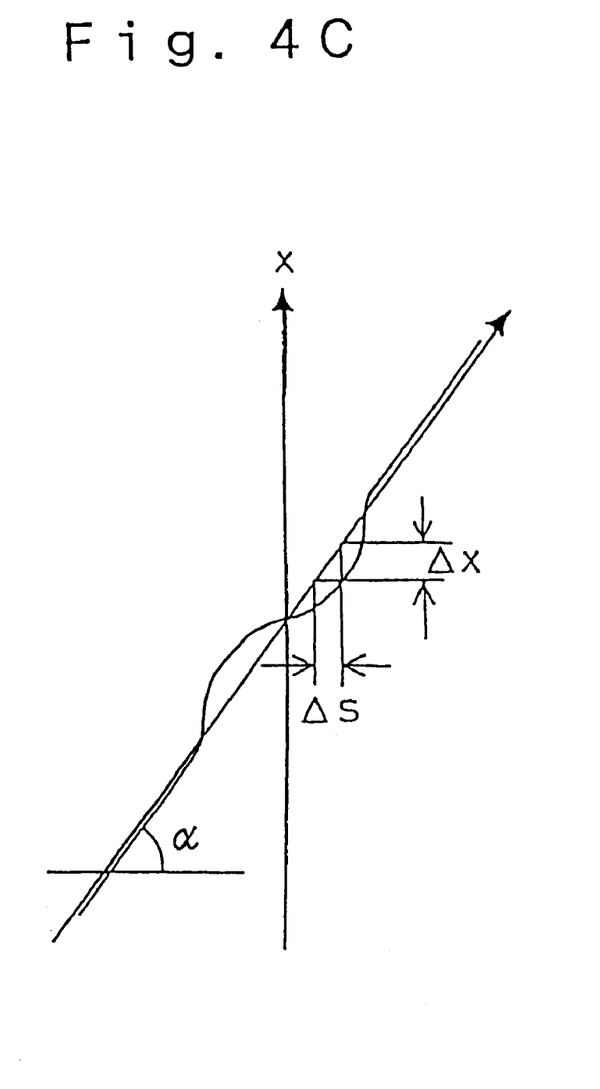
FIG. 4C is a view showing a photographed picture of the picture image and a border picture for finding a deflection quantity from the photographed picture.

If the ray is deflected and the position of the generating point deflects ΔS as shown in FIG. 4C, the deflection is converted to x axis using Δx=ΔS·tan α if α is used for inclination angle of the long side of the right-angled triangle. Then, if the edge of the long side of the right-angled triangle is taken out by picture image process as a border line of variable density and deflection quantity Δx of x direction of the border line, ΔS is determined by the following equation.

$$\Delta S = \Delta x / \tan \alpha \quad (6)$$

Figure 5:
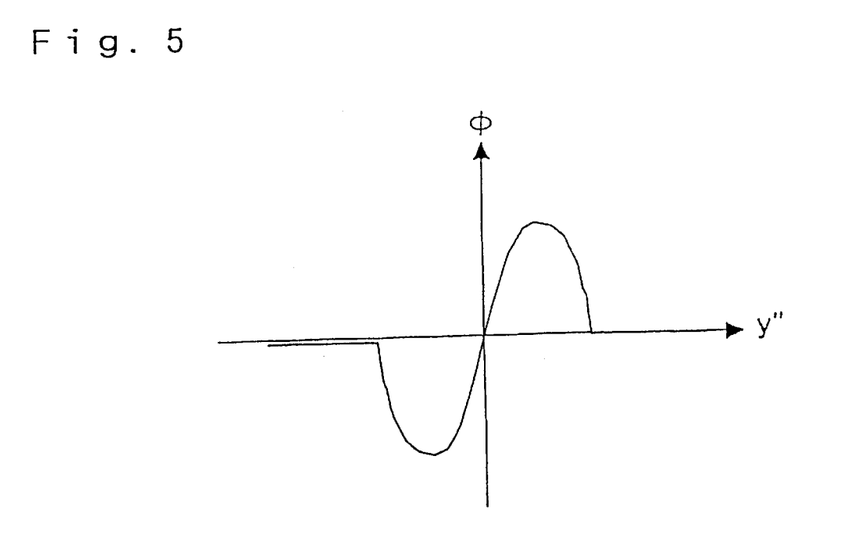
FIG. 5 is a view showing an example of a deflection function.

Using the value for calculations of equation (1) to equation (5), deflection function Φ(y″) is found. The example of the function is shown in FIG. 5. Using the function, distribution of reactive index n (r) is obtained applying the following conversion equation.

$$n(r) = n_1 [1/\pi) \int_r^k \{\Phi(y'')\} / \{\sqrt{(y''^2 - r^2)}\} dy''] \quad (7)$$

Figure 6:
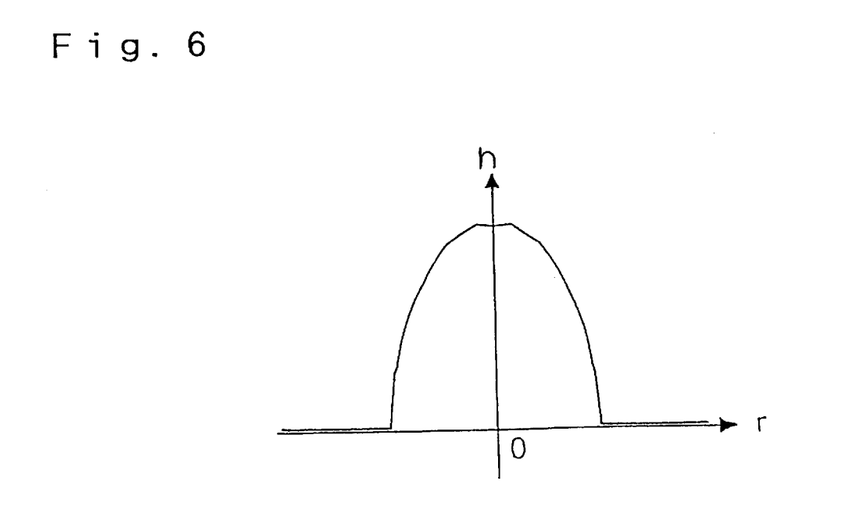
FIG. 6 is a view showing a distribution of reactive index found from the deflection function of FIG. 5.

Here, $n_1$ is reactive index of circumference (the matching liquid of reactive index 12) of the preform 21 of reference, r is a distance from center at cross section of the preform 21, and k is a range measured, which is ordinarily larger than radium of the preform 21. Therefore, there is the preform 21 in the matching liquid of reactive index 12. Value of reactive index at the point is $n_1$. The example of deflection function Φ(y″) found like the above-mentioned is shown in FIG. 5, and calculation result by equation (7) using the deflection function is shown in FIG. 6.

Measuring point deflects a little not only to y direction but x direction because measurement is carried out along a long side of the right-angle triangle determined to inclined direction. Although there is no problem when the preform 21 is uniform to x direction (axis direction) in the field of view, if correct distribution of reactive index in the vertical cross section of the preform 21 is found, it is required to measure at a condition in which x value is constant.

Here, the x driving stage 22 is formed like shown FIG. 2A and FIG. 3A in the present invention. Letting the preform 21 move up and down with whole of the column 11 attaching the preform 21 in the example of FIG. 2A and letting the preform 21 move right and left with whole of matching liquid cell of reactive index 13, measurement can be carried out changing the position along x axis of the preform 21 in the field of view of the picture image photographing unit 16.

By that, measurement becomes possible at the above-mentioned condition when measurement is carried out letting the preform 21 so that x value of the preform 21 comes a certain place. However, measuring time becomes long. Then, there is a method: shape of reactive index is found once by measuring the preform at the fixed state (it is measured along inclined line of the picture image 15), then new data is taken letting the preform move along x axis, and the data is modified by the new data at every data. According to the method, accuracy of measurement is improved at every taking out new data letting the preform 21 move. The method has advantage to select optimum combination of accuracy and measuring time required by a user because the measurement finishes in a short time if low accuracy is desired and it is possible to obtain result of high accuracy if long time measurement is permitted.

In the present embodiment, a deflection function is found by detecting a border of bright portion and dark portion in the picture image, that is edge portion by picture image process technique. However, the border is obscure so as to be hard to detect the edge because of diffraction effect when fine structure by sedimentary layer appearing often in the preform produced by a vapor-phase axial deposition (VAD) method or a chemical vapor deposition (CVD) method is formed. As above-mentioned, portions where deformation of the border by distribution of reactive index is projected to bright portion from dark portion and to the dark portion from the bright portion appear, and error may become large if the same threshold (discriminant value) for discriminating the border of the dark portion and the bright portion is used at the two conditions. Then, obtaining fragments of deflection function detecting edge using optimum threshold adapting each state, and these fragments become one deflection function connecting later. For example, a part of deflection function is found at the portion where the dark portion projects to the bright portion using $V_1$ for threshold, remaining part of deflection function is found at the portion where the bright portion projects to the dark portion using $V_2$ for threshold, and these are connected later. Actual value of $V_1$ and $V_2$ are determined by condition of the device, and these values belong to important know how of the present invention.

Figure 7A:
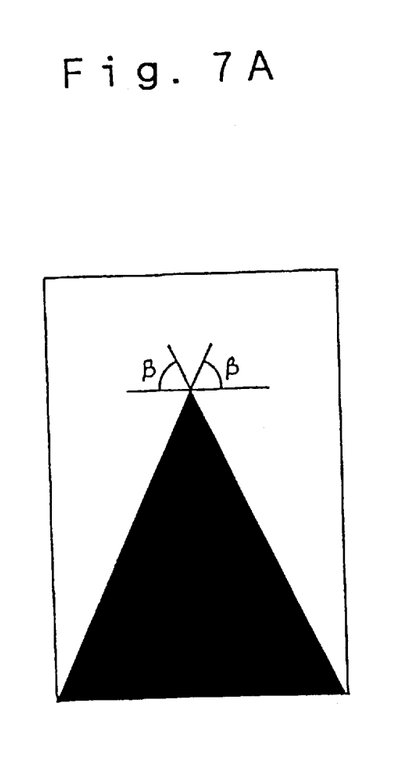
FIGS. 7A and 7B are examples of another picture image used for the method of measuring of the present invention.
Figure 7B:
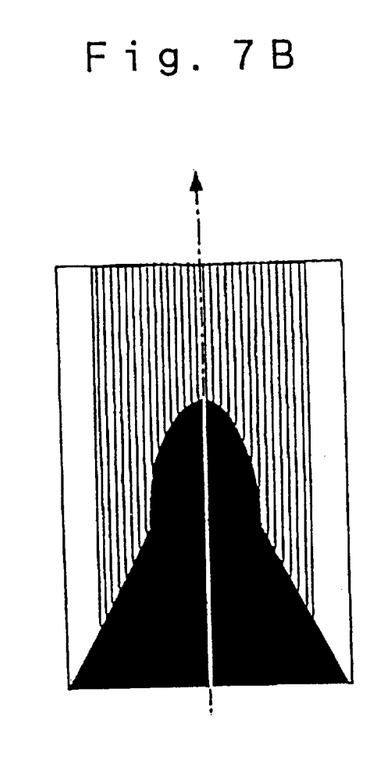
Figure 7C:
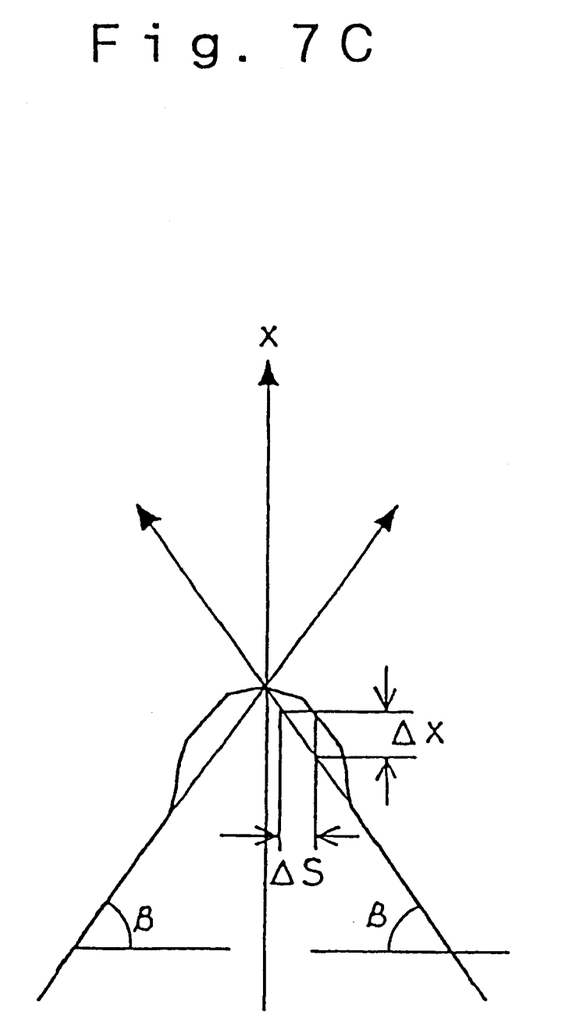
FIG. 7C is a view showing a photographed picture of the picture image and a border picture for finding a deflection quantity from the photographed picture.

FIGS. 7A and 7B are similar to FIGS. 4A and 4B of the embodiment using isosceles triangle picture image of two values (black and white) for picture image. In the picture image photographing vertex of the triangle, the picture image 16 is located so as to position at center of the preform 21. By such a locating, there is not coexistence of cases such that the dark portion projects to the bright portion like right-angle triangle and such that the bright portion projects to the dark portion, any of them can be limited. So it is no need to change threshold depending on the portion, whole of deflection function can be found using one threshold, and there is not trouble using right-angle triangle.

Figure 10A:
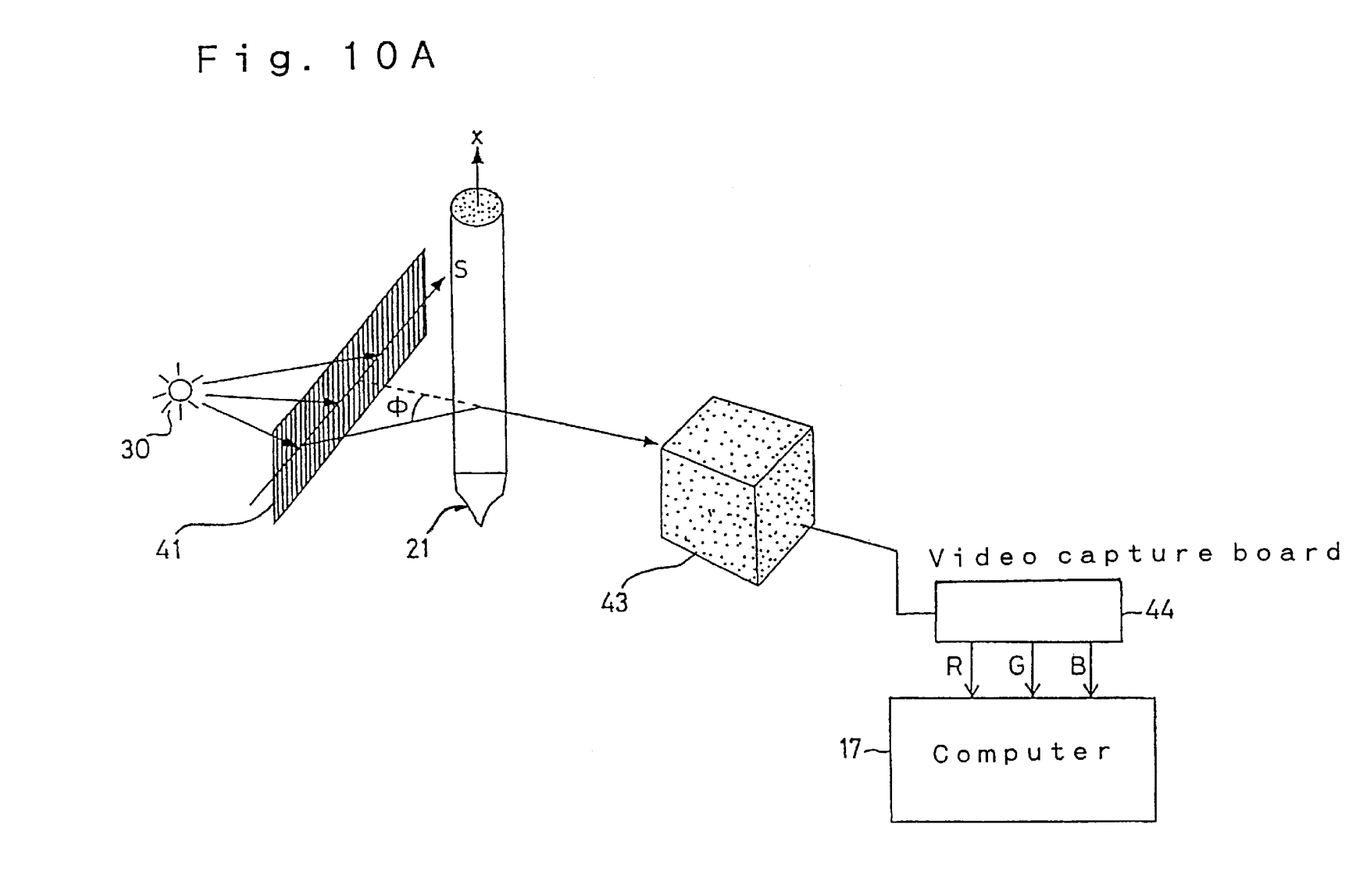
FIG. 10A is a view showing location of another embodiment using color of light.

Next, an embodiment using picture image in which hue (wavelength) changes straightly and continuously to y axis direction is shown. This system changes color (wavelength) of ray by generating position of ray in the picture images 6 and 15, the generating position can be determined by measuring color (wavelength) of the ray. Embodiments of this system are shown in FIG. 8 and FIG. 10A.

Figure 8:
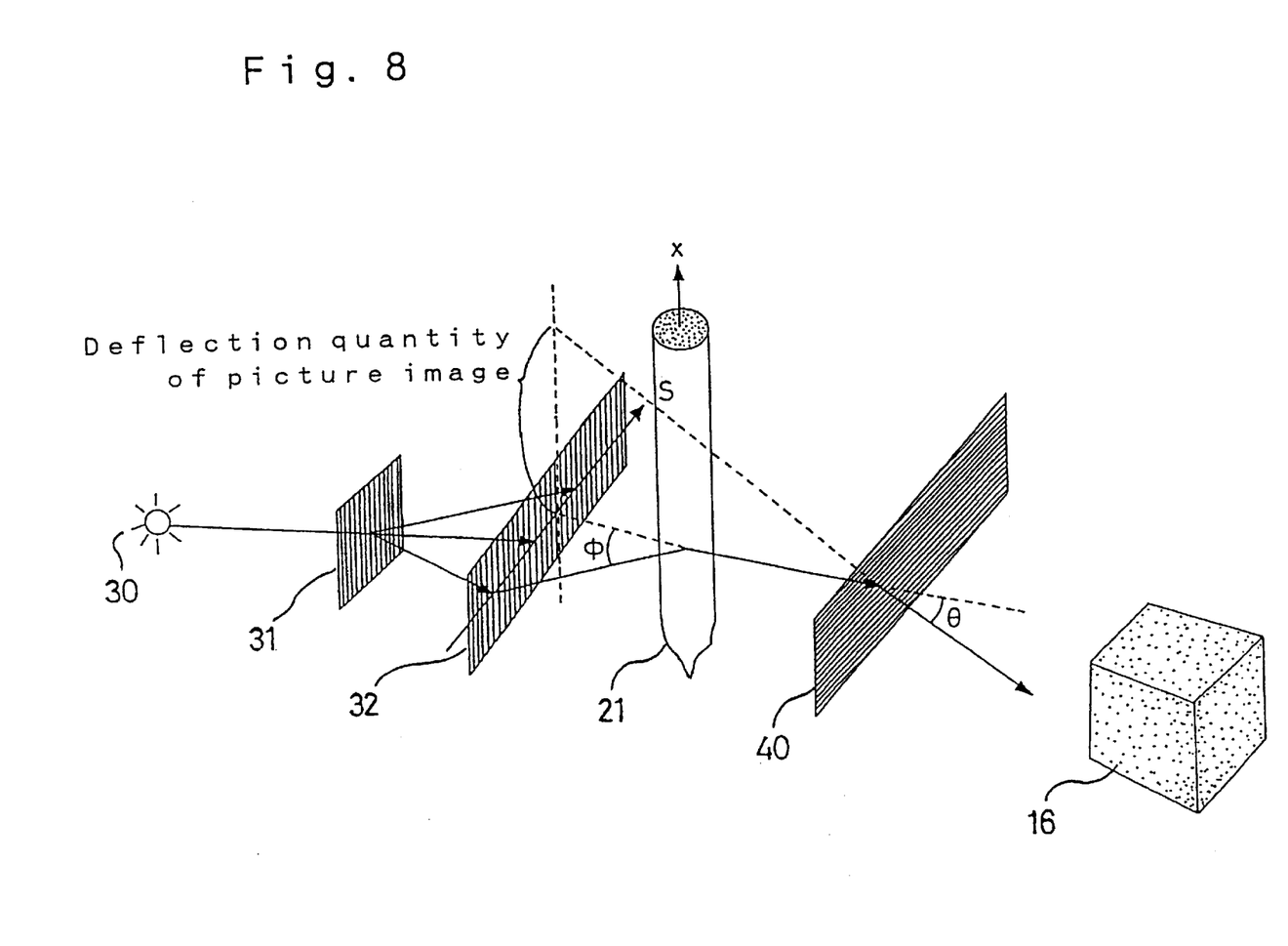
FIG. 8 is a view showing location of an embodiment of a device using picture image in which hue (wavelength) changes.

In the embodiment of FIG. 8, a ray from a white light source 30 is divided on S axis (y axis) in space by a diffraction grating 31, the ray is applied to a scattering screen 32, and the scattering screen is used as the picture image 6 or the picture image 15. The diffraction grating 31 can be replaced with a spectral prism.

Although the picture image 15 is photographed permeating the preform 21 by the photographing unit 16, at this time, the ray is diffracted to S axis (y axis) putting a scattering screen 40 (or a spectral prism) in front of the photographing unit 16. The ray applied to the scattering screen 40 deflects with diffraction angle θ according to the wavelength. Particularly primary diffraction ray conforms to the following equation.

$$\lambda/\Lambda = \sin \theta \qquad (8)$$

Here, $\lambda$ is wavelength of ray, and $\Lambda$ is period of the scattering screen 40. In the region where θ is small, θ approximates to proportion to $\lambda$. If wavelength changes continuously and linearly along y axis, diffraction angle θ too changes continuously and linearly so that the picture image is photographed deforming diagonally if the preform 21 is not set.

Figure 9:
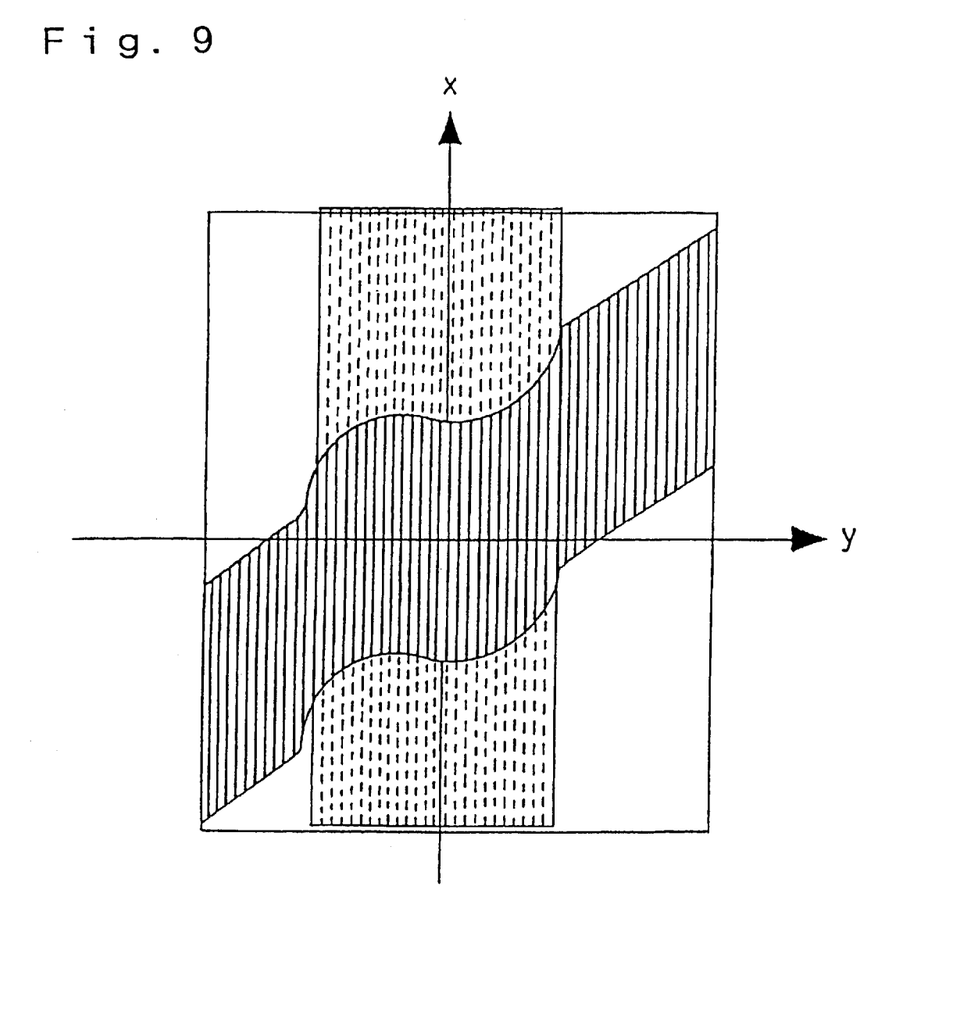
FIG. 9 is a view showing an example of a photographed picture obtained by the location of FIG. 8.

If generating position of the ray changes when the preform 21 is set, the change is transmitted as change of wavelength of the ray and the ray comes to position deflected in space so that the diagonal shape is further deformed. It is possible to find change of generating position of the ray from the changing quantity. An example of projected image obtained by this location is shown in FIG. 9. The method conducting change of position of the ray from deflection of picture image corresponds to the method of FIG. 4C.

Figure 10B:
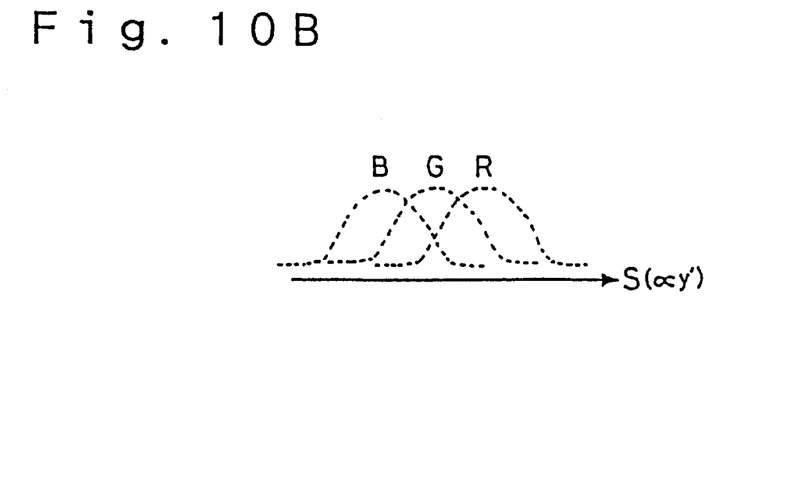
FIG. 10B is a view showing an example of a ratio of RGB distribution.
Figure 10C:
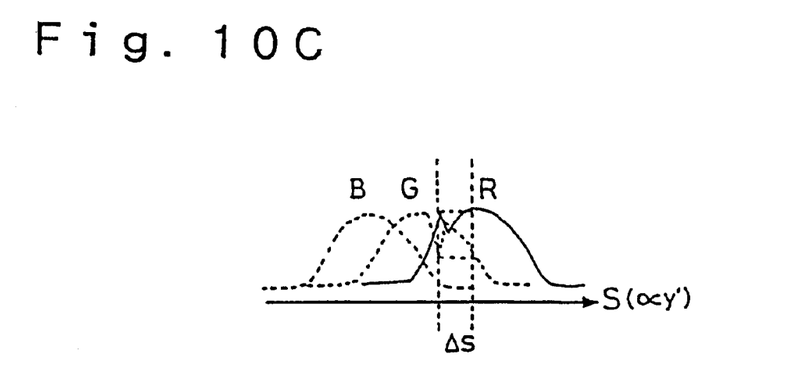
FIG. 10C is a view describing a method of presuming a starting position from data of deflection.

FIG. 10A shows a method using a color photographing unit 43 in another embodiment using color of ray. For a picture image 41, the picture image similar to the one used in FIG. 8 or color filter continuous and linear to S axis (y axis) about hue is used. Output of the color photographing unit 43 can be taken in the computer 17 dividing to R (red), G (green), and B (blue) through a video capture board 44, and color of ray is distinguished by distribution ratio. In another words, deflection of generating position of the ray is found from change of distribution ratio at each point generating when the preform 21 is set finding previously distribution ratio at each point when the preform 21 is not set. By finding deflection function from these data and carrying out numerical conversion with the same method as the above-mentioned, distribution of reactive index can be found. FIGS. 10A and 10B show an example of RGB distribution ratio at non-deflected photographed picture image and a method presuming generating position of the ray from deflection of RGB distribution ratio at deflected photographed picture image and the data.

Figure 11:
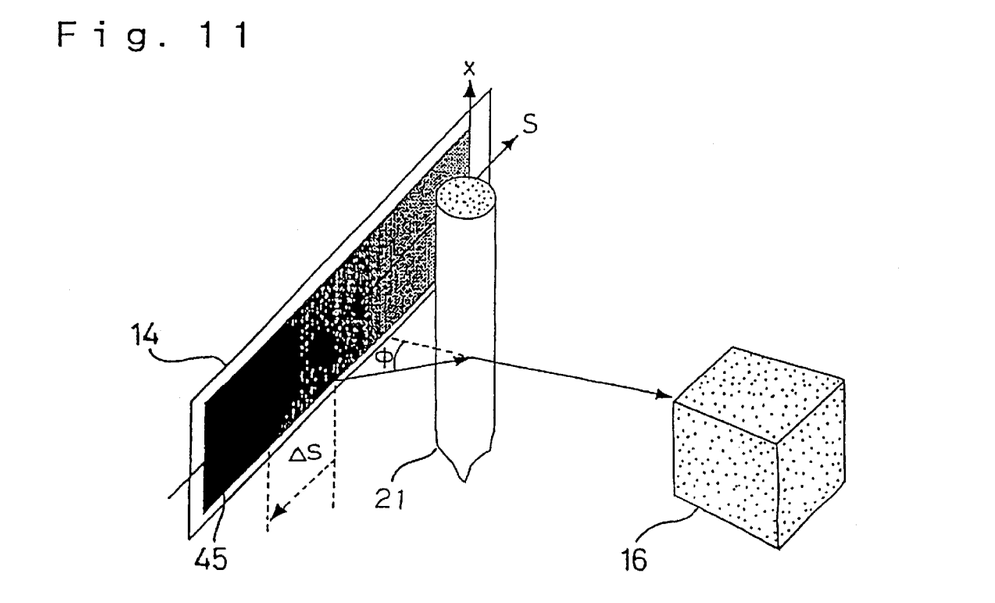
FIG. 11 is a view showing location of an embodiment of a device using an ND filter for picture image.
Figure 12:
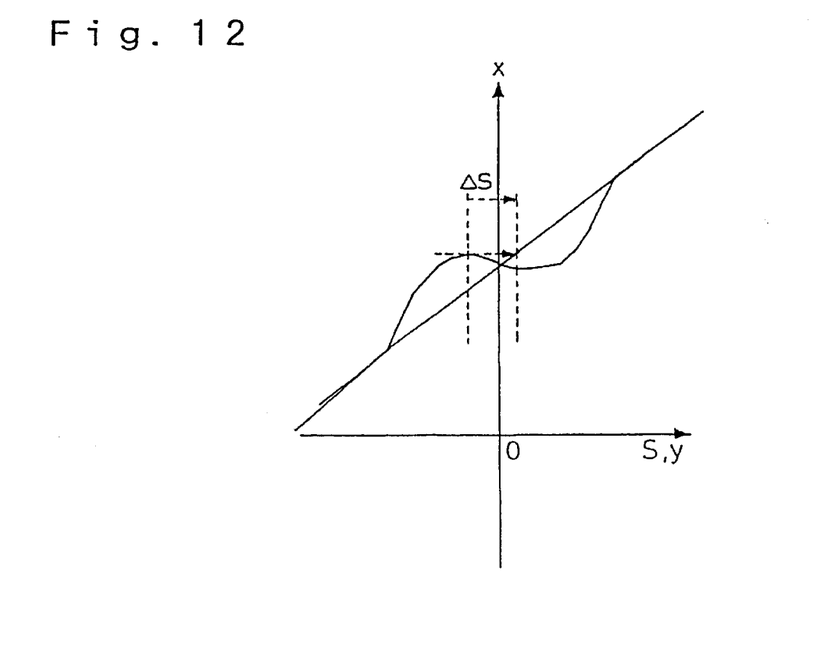
FIG. 12 is a view showing a curve of a deflected picture obtained from a photographed picture obtained from the location of FIG. 11.

Moreover, FIG. 11 shows an example of a neutral density (ND) filter 45 where transmittance changes linearly along S axis used for a picture image. An EL light source 14 is used for a light source. As transmittance changes when generating position of the ray deflects by measuring brightness of the picture image along y axis in the embodiment, a curve like FIG. 11 is obtained. Deflection quantity ΔS can be presumed from the curve using the similar method as the above-mentioned.

The method of measuring distribution of internal reactive index for preform of optical fiber and the measuring unit of the present invention is described in the embodiments. The present invention can be modified variously not limited by these embodiments. Although the above-mentioned embodiments are on the condition that deflected picture image is taken in the computer converting directly to projected image signal at the photographing unit, instead of that, the deflected picture image may be taken in the computer by photographing once with a picture photographing unit and by converting projected image using a scanner unit. A scattering board uneven in scattering characteristic can be located between the picture image and the light source for light source lighting the picture image except the EL board. Lighting the scattering board with light from white light source permeating the predetermined color filter or direct light from a coherent light source such as light-emitting diode and so on, the picture image may be lighted using the scattering board for secondary light source.

As cleared by the above-description, according to the method of measuring distribution of internal reactive index for the optical fiber preform and the measuring unit of the present invention, a picture image is located behind the optical fiber preform being cylindrical and having uneven distribution of reactive index at inside of the material, and the deflected picture of said image picture is photographed through the optical fiber preform. By analyzing the deflected picture of said picture image, a deflection function is found, and distribution of reactive index of the optical fiber preform is found based on the deflection function. Therefore, photographing of a picture image is possible so as to photograph the deflected picture if the preform is a high NA optical fiber preform and angle of deflection of permeating ray becomes large. Therefore, even high NA optical fiber preform difficult in measuring by the conventional method can measure distribution of reactive index accurately, and that contributes to improvement of performance of optical fiber so as to contribute development of intelligent society.

What is claimed is:

1. A method of measuring the internal refractive index distribution for an optical fiber preform, comprising the steps of: providing the optical fiber preform having an uneven internal refractive index distribution; locating a picture image at a first side of the optical fiber preform, the picture image having a preselected pattern containing position data; photographing a deflected picture of the picture image through the optical fiber preform using a photographing unit disposed at a second side of the optical fiber preform opposite the first side of the optical fiber preform; obtaining a deflection function by analyzing the deflected picture of the picture image by ray tracing the deflected picture of the picture image; and measuring the internal refractive index distribution of the optical fiber preform in accordance with the obtained deflection function.

2. A method according to claim 1; further comprising the step of lighting the picture image with an incoherent light source.

3. A method according to claim 1; wherein the locating step comprises locating a binary picture image of a right-angled triangle.

4. A method according to claim 3; wherein the obtaining step comprises detecting an entire variable density border line of the picture image using different threshold values, and obtaining a deflection distribution of the picture image in accordance with the detected border line.

5. A method according to claim 1; wherein the locating step comprises locating a binary picture image of an isosceles triangle.

6. A method according to claim 1; wherein the locating step comprises locating a picture image having a continuously changing hue or wavelength.

7. A method of measuring the internal refractive index distribution for an optical fiber preform, comprising the steps of: providing the optical fiber preform having an uneven internal refractive index distribution; locating a picture image at a first side of the optical fiber preform, the picture image having a preselected pattern containing position data; lighting the picture image with an incoherent light source; photographing a deflected picture of the picture image through the optical fiber preform using a photographing unit disposed at a second side of the optical fiber preform opposite the first side of the optical fiber preform; obtaining a deflection function by analyzing the deflected picture of the picture image by ray tracing the deflected picture of the picture image; and measuring the internal refractive index distribution of the optical fiber preform in accordance with the obtained deflection function.

8. A method according to claim 7; wherein the locating step comprises locating a binary picture image of a right-angled triangle.

9. A method according to claim 8; wherein the obtaining step comprises detecting an entire variable density border line of the picture image using different threshold values, and obtaining a deflection distribution of the picture image in accordance with the detected border line.

10. A method according to claim 7; wherein the locating step comprises locating a binary picture image of an isosceles triangle.

11. A method according to claim 7; wherein the locating step comprises locating a picture image having a continuously changing hue or wavelength.

12. A measuring device for measuring the internal refractive index distribution of an optical tiber preform, the measuring device comprising: means for generating a picture image having a preselected pattern containing position data; an incoherent light source for lighting the picture image; a supporting unit for supporting the optical fiber preform having an uneven internal refractive index distribution; a photographing unit for photographing a deflected picture of said picture image through the optical fiber preform; and means for obtaining a deflection function from the photographed deflected picture by ray tracing the deflected picture of the picture image and for measuring the internal refractive index distribution of the optical fiber preform in accordance with the deflection function.

13. A measuring device according to claim 12; wherein the incoherent light source comprises a light source and a scattering board located in front of the light source.

14. A measuring device according to claim 13; wherein the photographing unit has a diaphragm for limiting the amount of light entering the photographing unit.

15. A measuring device according to claim 14; wherein the photographing unit has a mask through which only light having a preselected wavelength enters the photographing unit.

16. A measuring device according to claim 14; wherein the photographing unit has a filter through which only light having a preselected wavelength enters the photographing unit.

17. A measuring device according to claim 12; wherein the incoherent light source comprises an electroluminescence board.

18. A measuring device according to claim 17; wherein the photographing unit has a diaphragm for limiting the amount of light entering the photographing unit.

19. A measuring device according to claim 18; wherein the photographing unit has a mask through which only light having a preselected wavelength enters the photographing unit.

20. A measuring device according to claim 18; wherein the photographing unit has a filter through which only light having a preselected wavelength enters the photographing unit.

21. A measuring device according to claim 12; wherein the photographing unit has a diaphragm for limiting the amount of light entering the photographing unit.

22. A measuring device according to claim 21; wherein the photographing unit has a mask through which only light having a preselected wavelength enters the photographing unit.

23. A measuring device according to claim 21; wherein the photographing unit has a filter through which only light having a preselected wavelength enters the photographing unit.

24. A measuring device according to claim 12; wherein the picture image comprises a binary picture image of a right-angled triangle.

25. A measuring device according to claim 24; wherein the means for obtaining the deflection function includes means for detecting an entire variable density border line of the picture image using different threshold values and for obtaining a deflection distribution of the picture image in accordance with the detected border line.

26. A measuring device according to claim 12; wherein the picture image comprises a binary picture image of an isosceles triangle.

27. A measuring device according to claim 12; wherein the picture image has a continuously changing hue or wavelength.

28. A measuring device for measuring the internal refractive index distribution of an optical fiber preform, the measuring device comprising:
  a supporting unit for supporting the optical fiber preform having an uneven internal reactive index distribution;
  means for locating a picture image at a first side of the optical fiber preform, the picture image having a preselected pattern containing position data;
  a photographing unit disposed at a second side of the optical fiber preform opposite the first side of the optical fiber preform for photographing a deflected picture of the picture image through the optical fiber preform;
  means for obtaining a deflection function from the photographed deflected picture; and
  means for measuring the internal refractive index distribution of the optical fiber preform in accordance with the deflection function.

29. A measuring device according to claim 28; further comprising an incoherent light source for lighting the picture image.

* * * * *